United States Patent [19]
Lazarevski et al.

[11] Patent Number: 6,110,965
[45] Date of Patent: Aug. 29, 2000

[54] KETOLIDES FROM THE CLASS OF 15-MEMBERED LACTAMS

[75] Inventors: Gorjana Lazarevski; Gabrijela Kobrehel; Željko Kelnerić, all of Zagreb, Croatia

[73] Assignee: PLIVA, farmaceutska, kemijska, prehrambena i kozmeticka industrija, dionicko drustvo, Zagreb, Croatia

[21] Appl. No.: 09/127,764

[22] Filed: Jul. 31, 1998

[30] Foreign Application Priority Data

Apr. 6, 1998 [HR] Croatia .................. P980189A

[51] Int. Cl.[7] .............. A61K 31/35; C07D 267/00; A61P 31/04
[52] U.S. Cl. .......................... 514/459; 540/454
[58] Field of Search ............... 514/459; 540/454

[56] References Cited

U.S. PATENT DOCUMENTS 5,202,434  4/1993  Wilkening .................. 540/454

OTHER PUBLICATIONS

Waddell et al., Synthesis and Antibacterial Activity of O–methyl Derivatives of Azalide Antibiotics, Bioorganic & Medicinal Chemisty Letters, vol. 8, No. 11, pp. 1321–1326, Jun. 1998.

*Primary Examiner*—Richard L. Raymond
*Assistant Examiner*—Brenda Coleman
*Attorney, Agent, or Firm*—Pollock, Vande Sande & Amernick

[57] ABSTRACT

The present invention relates to the new 15-membered ketoazalides from the class of 6-O-methyl-8a-aza-8a-homo- and 6-O-methyl-9a-aza-9a-homoerythromycin A with the general formula (I)

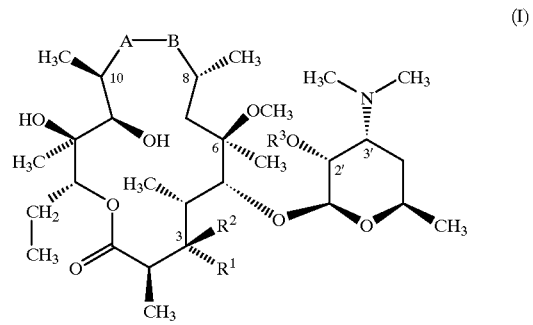

wherein

A represents NH group and B at the same time represents C=O group, or

A represents C=O group and B at the same time represents NH group, $R^1$ represents OH group, L-cladinosyl group of the formula (II)

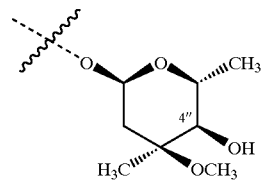

or together with $R^2$ represents ketone, $R^2$ represents hydrogen or together with $R^1$ represents ketone, $R^3$ represents hydrogen or $C_1$–$C_4$ alkanoyl group, to intermediates and a process for their preparation, to their pharmaceutically acceptable addition salts with inorganic or organic acids, to the process for the preparation of pharmaceutical compositions, as well as to the use of pharmaceutical compositions for treating bacterial infections.

22 Claims, No Drawings

KETOLIDES FROM THE CLASS OF 15-MEMBERED LACTAMS

TECHNICAL FIELD

International Patent Classification: A 61 K 31/70, C 07 H 17/08

1. Technical Problem

The present invention relates to new compounds of erythromycin A macrolide antibiotics class. Especially, it relates to new 15-membered ketoazalides of the class of 6-O-methyl-8a-aza-8a-homo- and 6-O-methyl-9a-aza-9a-homoerythromycin A, to intermediates and a process for their preparation, to their pharmaceutically acceptable addition salts with inorganic and organic acids, to a process for the preparation of pharmaceutical compositions as well as to the use of pharmaceutical compositions in the treatment of bacterial infections.

2. Prior Art

Erythromycin A is a macrolide antibiotic, whose structure is characterized by a 14-membered lactone ring having C-9 ketone and two sugars, L-cladinose and D-desosamine, which are glycosidically bound at C-3 and C-5 positions to the aglycone part of the molecule (McGuire: Antibiot. Chemother., 1952, 2: 281). For more than 40 years erythromycin A has been considered to be a safe and active antimicrobial agent for treating respiratory and genital infections caused by gram-positive bacteria of the strains like Legionella, Mycoplasma, Chlamidia and Helicobacter. The observed changes in bioavailability after the application of oral preparations, gastric intolerance in many patients and the loss of activity in an acidic medium are the main disadvantages of the therapeutical use of erythromycin A. The spirocyclization of aglycone ring is successfully inhibited by the chemical transformation of C-9 ketone or of hydroxyl groups at C-6 and/or C-12 position. Thus e.g. by oximation of C-9 ketone of erythromycin A with hydroxylamine hydrochloride, Beckmann's rearrangement of the obtained 9(E)-oxime and reduction of the thus formed 6,9-imino ether (6-deoxy-9-deoxo-9a-aza-9a-homoerythromycin A 6,9-cyclic imino ether), there was obtained 9-deoxo-9a-aza-9a-homoerythromycin A, the first semisynthetic macrolide having a 15-membered azalactone ring (Kobrehel G. et al., U.S. Pat. No. 4,328,334, May 1982). By reductive methylation of the newly introduced endocyclic 9a-amino group according to Eschweiler-Clark process, 9-deoxo-9a-methyl-9a-aza-9a-homoerythromycin A (AZITHROMYCIN), a prototype of a new azalide antibiotics class was synthesized (Kobrehel G. et al., BE 892 357, July 1982). In addition to the broad antimicrobial spectrum including gram-negative bacteria, azithromycin is also characterized by a long biological half-time, a specific transport mechanism to the site of application and a short therapy period. Azithromycin is able to penetrate and to accumulate within human phagocyte cells, which results in an improved action upon intracellular pathogenic microorganisms of the strains Legionella, Chlamydia and Helicobacter.

Further, it is known that C-6/C-12 spirocyclization of erythromycin A is also inhibited by O-methylation of C-6 hydroxyl group of aglycone ring (Watanabe Y. et al., U.S. Pat. No. 4,331,803, May 1982). By reaction of erythromycin A with benzyloxycarbonyl chloride followed by methylation of the obtained 2'-O,3'-N-bis(benzyloxycarbonyl)-derivative, elimination of the protecting groups and 3'-N-methylation, 6-O-methyl-erythromycin A (CLARITHROMYCIN) (Morimoto S. et al., J. Antibiotics 1984, 37, 187) is formed. If compared to erythromycin A, clarithromycin is considerably more stable in acidic medium and shows an increased in vitro activity against gram-positive bacterial strains (Kirst H. A. et al, Antimicrobial Agents and Chemother., 1989, 1419).

New investigations on 14-membered macrolides have led to a new type of macrolide antibiotics, namely ketolides, characterized by 3-keto group instead of neutral sugar L-cladinose, the latter being well-known for its instability even in a weakly acidic medium (Agouridas C. et al., EP 596802 A1, May 1994, Le Martret O., FR 2697524 A1, May 94). Ketolides exibit significantly improved in vitro activity against MLS (macrolide, lincosamide and streptogramine B) induced by resistant organisms (Jamjian C., Antimicrob. Agents Chemother., 1997, 41, 485).

According to the known and established prior art, 15-membered ketoazalides from the class of 6-O-methyl-8a-aza-8a-homo- and 6-O-methyl-9a-aza-9a-homoerythromycin A and their pharmaceutically acceptable addition salts with organic or inorganic acids, methods and intermediates for their preparation as well as methods for the preparation of pharmaceutical preparations and the use thereof have hitherto not been described.

The object of the present invention is represented by Beckmann's rearrangement of 9(E)- and 9(Z)-oxime of 6-O-methylerythromycin A, hydrolysis of cladinose in thus obtained 8a- and 9a-lactams, protection of hydroxyl groups in 2'-position of desosamine, oxidation of the 3-hydroxyl group and removal of protecting groups, whereby new, hitherto not described 15-membered ketoazalides from the class of 6-O-methyl-8a-aza-8a-homo- and 6-O-methyl-9a-aza-9a-homoerythromycin A are obtained.

TECHNICAL SOLUTION

New 15-membered ketoazalides from the class of 6-O-methyl-8a-aza-8a-homo- and 6-O-methyl-9a-aza-9a-homoerythromycin A with the general formula (I)

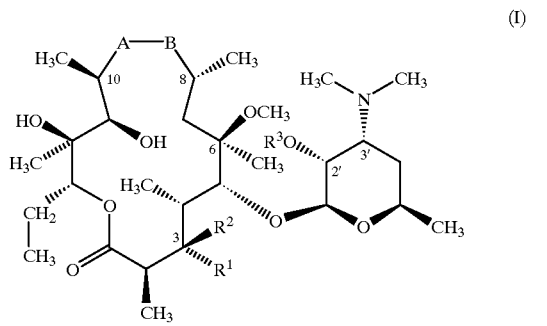

(I)

wherein

A represents NH group and B at the same time represents C=O group, or

A represents C=O group and B at the same time represents NH group, $R^1$ represents OH group, L-cladinosyl group of the fonnula (II)

(II)

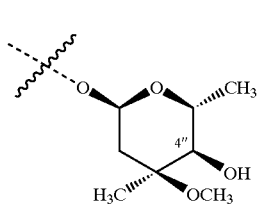

or together with R² represents ketone,

R² represents hydrogen or together with R¹ represents ketone,

R³ represents hydrogen or C₁–C₄ alkanoyl group, and their pharmaceutically acceptable addition salts with inorganic or organic acids are obtained as follows.

Step 1:

The first step of the invention includes oximation of C-9 ketone of 6-O-methylerythromycin A (clarithromycin) of the formula (III)

(III)

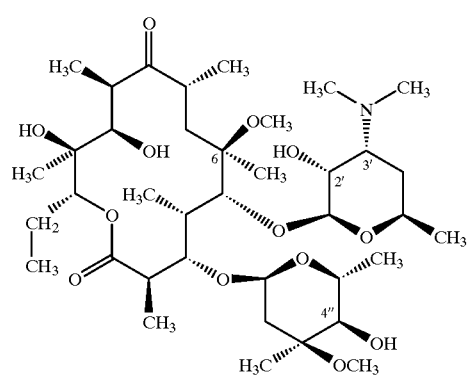

into the corresponding oxime. The conversion of ketone into oxime is a well-known reaction usually performed with hydroxylamine hydrochloride in the presence of appropriate inorganic or organic bases in a suitable protic or aprotic solvent. Hydroxylamine hydrochloride is used in a 1 to 15-equimolar excess, preferably in a 10-equimolar excess with regard to clarithromycin. As suitable bases alkali hydroxides, carbonates, hydrogen carbonates and acetates are used whereas as solvents C₁–C₃ alcohols are used. The preferred base is sodium carbonate or sodium acetate and the preferred solvent is methanol. In general, the reaction is performed at a temperature from 0 to 80° C., preferably at 65° C., within 2 hours to a few days, but mainly it is accomplished within 8 to 20 hours. The treatment is performed in the usual manner, e.g. by evaporation of the solvent under vacuum, addition of a mixture of water and organic solvent followed by extraction in an alkaline medium, preferably at pH 8.0–10.0. As solvents for the extraction of the product methylene chloride, chloroform, ethyl acetate, diethylether and toluene are used, with chloroform being the preferred one. The product is isolated by the separation of the organic layer and evaporation of the solvent, which yields a mixture of 6-O-methylerythromycin A 9(E)- and 9(Z)-oxime of the formula (IV)

(IV)

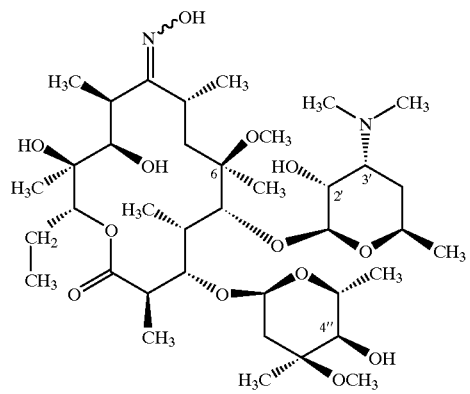

in a ratio of about 1:1. If necessary, the separation of the isomers is performed by chromatography on a silica gel column by using the system methylene chloride-methanol-ammonium hydroxide 90:9:1.5, which yields a chromatographically homogeneous 6-O-methyl-erythromycin A 9(E)-oxime with Rf 0.446 of the formula (IVa)

(IVa)

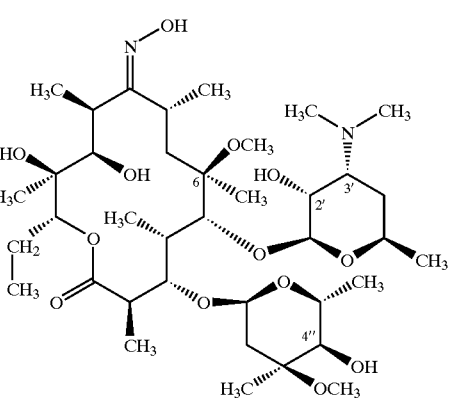

and chromatographically homogeneous 6-O-methylerythromycin A 9(Z)-oxime with Rf 0.355 of the formula (IVb)

(IVb)

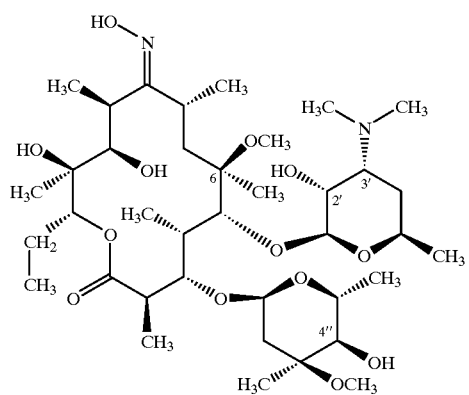

Step 2:

Conversion of 6-O-methyl-erythromycin A 9(E)-oxime of formula (IVa) into 6-O-methyl-9a-aza-9a-homoerythromycin A of the general formula (I)

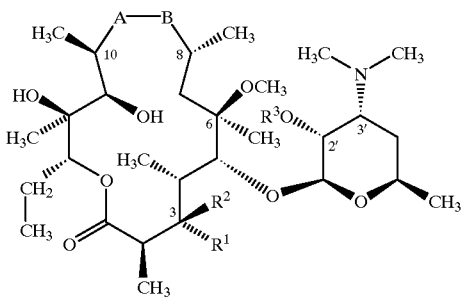

wherein A represents NH group, B at the same time represents C=O group, R¹ represents L-cladinosyl group of the formula (II)

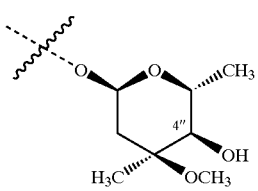

R² and R³ are the same and represent hydrogen,
is performed by the reaction of Beckmann's rearrangement (see "Comprehensive Organic Chemistry", I.O. Sutherland (Ed.), Pergamon Press, New York, 1979, Vol. 2, 398–400 and 967–968). In general, Beckmann's rearrangement of ketoxime leads to carboxamide or, in the case of cyclic systems, to lactams. The rearrangement mechanism includes a preliminary conversion of oxime hydroxyl into a better leaving group, which in a second reaction step is cleaved off under a simultaneous migration of the carbon atom in the anti-position with regard to the leaving group. In an aqueous medium as an intermediate a nitrilium ion is formed, which reacts with water yielding an appropriate amide.

The reaction of Beckmann's rearrangement is performed under acidic, neutral and basic conditions. Common acidic reagents catalyzing the rearrangement include conc. sulfuric acid, polyphosphoric acid, tionyl chloride, phosphoric pentachloride, sulfur dioxide and formic acid. Due to the sensibility of macrolide molecule in an acidic medium and especially due to the ease of cleavage of neutral sugar L-cladinose, these reagents are not suitable for the rearrangement of oxime of the formula (IVa) into 6-O-methyl-9a-aza-9a-homoerythromycin A of the general formula (I), wherein A, B, R¹, R², and R³ have the above-mentioned meanings. Preferably, Beckmann's rearrangement of oxime (IVa) is performed by initial O-sulfonation of oxime hydroxyl with alkylsulfonyl halides, arilsulfonyl halides or arilsulfonyl anhydrides. Intermediate oxime sulfonate is isolated or, usually, the rearrangement into the desired product is performed in situ. Generally, sulfonation and rearrangement are performed in the presence of organic or inorganic bases.

The preferred sulfonation reagents catalyzing the rearrangement of oxime (IVa) include methansulfonyl chloride, benzenesulfonyl chloride, 4-acetylamidosulfonyl chloride, p-toluensulfonyl chloride, anhydrides of benzenesulfonic and p-toluene-sulfonic acid. The reaction is performed in the presence of inorganic bases such as sodium hydrogen carbonate or potassium carbonate or in presence of organic bases such as pyridine, 4-dimethylaminopyridine, triethylamine and N,N-diisopropyl-amine. Suitable solvents include aqueous mixtures such as acetone-water mixture and dioxan-water mixture, and organic solvents such as methylene chloride, chloroform, ethyl acetate, diethyl ether, tetrahydrofuran, toluene, acetonitrile and pyridine. Generally, the reaction is performed by the use of 1–3 equimolar excess of the sulfonation reagent and with the same or greater equimolar amount of the base at a temperature from −20 to 50° C. Pyridine is often used as the solvent and as the base at the same time. Preferably, Beckmann's rearrangement of oxime (IVa) is performed in an acetone-water mixture with a double equimolar excess of p-toluensulfochloride and sodium hydrogen carbonate. If necessary, the product is purified by chromatography on a silica gel column by the use of the solvent system methylene chloride-methanol-ammonium hydroxide 90:9:1.5, yielding a chromatographically homogeneous 6-O-methyl-9a-aza-9a-homoerythromycin A.

Beckmann's rearrangement of 6-O-methylerythromycin A 9(Z)-oxime of the formula (IVb) into 6-O-methyl-8a-aza-8a-homoerythromycin A of the general formula (I), wherein A represents C=O group, B at the same time represents NH group, R¹ represents L-cladinosyl group of the formula (II), and R² and R³ are the same and represent hydrogen, is performed in analogous manner as with 9(E)-oxime (IVa).

Step 3:

6-O-methyl-9a-aza-9a-homoerythromycin A or 6-O-methyl-8a-aza-8a-homoerythromycin A of Step 2 of the general formula (I), wherein A, B, R¹, R² and R³ have the above-mentioned meanings, are subjected, if appropriate, to the action of strong acids, preferably 0.25–1.5 N hydrochloric acid, at room temperature within 10–30 hours, yielding 3-O-decladinosyl-3-oxy-derivatives of 6-O-methyl-9a-aza-9a-homoerythromycin A or 6-O-methyl-8a-aza-8a-homoerythromycin A of the general formula (I), wherein A represents NH group and B at the same time represents C=O group, or A represents C=O group and B at the same time represent NH group, R¹ represents OH group, and R² and R³ are the same and represent hydrogen.

Step 4:

3-O-decladinosyl-3-oxy-6-O-methyl-9a-aza-9a-homoerythromycin A or 6-O-methyl-8a-aza-8a-homoerythromycin A of Step 3 of the general formula (I), wherein A, B, R¹, R² and R³ have the above-mentioned meanings, are subjected, if appropriate, to the reaction of selective acylation of hydroxyl group at 2'-position of desosamine. Acylation is performed by the use of anhydrides of carboxylic acids having up to 4 carbon atoms, preferably with acetic acid anhydride, in the presence of inorganic or organic bases in an inert organic solvent at a temperature from 0 to 30° C. yielding 3-decladinosyl-3-oxy-6-O-methyl-9a-aza-9a-homoerythromycin A 2'-O-acetate or 3-decladinosyl-3-oxy-6-O-methyl-8a-aza-8a-homoerythromycin A 2'-O-acetate of the general formula (I), wherein A represents NH group and B at the same time represents C=O group, or A represents C=O group and B at the same time represent NH group, R¹ represents OH group, R² is hydrogen and R³ is acetyl. As appropriate bases sodium hydrogen carbonate, sodium carbonate, potassium carbonate, triethylamine, pyridine, tributylamine, preferably sodium hydrogen carbonate are used. As a suitable inert solvent methylene chloride, dichloro ethane, acetone, pyridine, ethyl acetate, tetrahydrofuran, preferably methylene chloride are used.

Step 5:

3-decladinosyl-3-oxy-6-O-methyl-9a-aza-9a-homoerythromycin A-2' O-acetate or 3-decladinosyl-3-oxy- 6-O-methyl-8a-aza-8a-homoerythromycin A-2' O-acetate of Step 4 of the general formula (I), wherein A, B, $R^1$, $R^2$ and $R^3$ have the above-mentioned meanings, are subjected, if appropriate, to an oxidation of the hydroxyl group at C-3 position of aglycone ring according to the modified Moffat-Pfitzner process with N,N-dimethylaminopropyl-ethyl-carbodiimide in the presence of dimethylsulfoxide and pyridinium trifluoroacetate as a catalyst, in an inert organic solvent, preferably in methylene chloride, at a temperature from 10° C. to room temperature, yielding 3-decladinosyl-3-oxo-6-O-methyl-9a-aza-9a-homoerythromycin A 2'-O-acetate or 3-decladinosyl-3-oxo-6-O-methyl-8a-aza-8a-homoerythromycin A 2'-O-acetate of the general formula (I), wherein A represents NH group and B at the same time represents C=O group, or A represents C=O group and B at the same time represents NH group, $R^1$ and $R^2$ together represent ketone and $R^3$ represents acetyl group.

Step 6:

3-decladinosyl-3-oxo-6-O-methyl-9a-aza-9a-homoerythromycin A 2'-O-acetate or 3-decladinosyl-3-oxo-6-O-methyl-8a-aza-8a-homoerythromycin A 2'-O-acetate of Step 5 of the general formula (I), wherein A, B, $R^1$, $R^2$ and $R^3$ have the above-mentioned meanings, are then subjected to solvolysis in lower alcohols, preferably in methanol, at a temperature from room temperature to the reflux temperature of the solvent, yielding 3-decladinosyl-3-oxo-6-O-methyl-9a-aza-9a-homoerythromycin A or 3-decladinosyl-3-oxo-6-O-methyl-8a-aza-8a-homoerythromycin A of the general formula (I), wherein A represents NH group and B at the same time represents C=O group, or A represents C=O group and B at the same time represent NH group, $R^1$ and $R^2$ together represent ketone and $R^3$ represents hydrogen.

Pharmaceutically acceptable addition salts, which are also an object of the present invention are obtained by the reaction of new compounds from the class of 6-O-methyl-8a-aza-8a-homoerythromycin A and 6-O-methyl-9a-aza-9a-homoerythromycin A of the general formula (I), wherein A, B, $R^1$, $R^2$ and $R^3$ have the above-mentioned meanings, with at least equimolar amount of an appropriate inorganic or organic acid such as hydrochloric, hydroiodic, sulfuric, phosphoric, acetic, propionic, trifluoroacetic, maleic, citric, stearic, succinic, ethylsuccinic, methanesulfonic, benzenesulfonic, p-toluenesulfonic and laurylsulfonic acids in a solvent inert to the reaction. The addition salts are isolated by filtration if they are insoluble in a solvent inert to the reaction, by precipitation with a non-solvent or by evaporation of the solvent, mostly by method of lyophilization.

Antibacterial in vitro action of the new compounds of the general formula (I), wherein A, B, $R^1$, $R^2$ and $R^3$ have the above-mentioned meanings, and of their pharmaceutically acceptable addition salts with inorganic or organic acids was determined on a series of standard test microorganisms and clinical isolates by microdilution process according to the protocol NCCLS (The National Commitee for Clinical Laboratory Standards, Document M7-A2, Vol. 10, No. 8, 1990 and Document M11-A2, Vol. 10, 15,1991). The control of the laboratory process was performed by means of control strain *Staphyloccocus aureus* ATTC 29213 (The American Type Culture Collection) according to protocol NCCLS (Document M7-A2, Table 3, M100-S4).

The antibacterial in vitro action on a series of standard test microorganisms for 6-O-methyl-8a-aza-8a-homoerythromycin A from Example 3 in comparison with azithromycin, erythromycin and clarithromycin is represented in Table 1.

TABLE 1

Antibacterial in vitro action (MIC, mg/l) of 6-O-methyl-8a-aza-8a-homo-erythromycin A (Example 3) in comparison with azithromycin (Az), erythromycin (Er) and clarithromycin (Cl)

| Test microorganism | Az | Er | Cl | Example 3 |
|---|---|---|---|---|
| Listeria monocytogenes ATCC 7644 | <0.125 | <0.125 | <0.125 | <0.125 |
| Staphylococcus aureus ATCC 25923 | 0.5 | 0.25 | 0.5 | 0.5 |
| Staphylococcus epidermidis ATCC 12228 | 1.0 | 0.25 | 0.25 | 0.5 |
| Enterococcus faecalis ATCC 35550 | 0.5 | 1.0 | 0.25 | 1.0 |
| Streptococcus pneumoniae ATCC 6305 | <0.125 | <0.125 | <0.125 | <0.125 |
| Streptococcus pyogenes ATCC 19615 | <0.125 | <0.125 | <0.125 | <0.125 |
| Clostridium perfringens ATCC 13124 | 0.125 | 0.5 | 0.125 | 0.25 |
| Moraxella catarrhalis ATCC 25238 | <0.125 | <0.125 | <0.125 | <0.125 |
| Campylobacter fetus ATCC 19438 | <0.125 | <0.125 | <0.125 | <0.125 |
| Campylobacter jejuni ATCC 33291 | <0.125 | <0.125 | <0.125 | <0.125 |
| Citroobacter freundii ATCC 8090 | 4.0 | 64.0 | 64.0 | 16.0 |
| Escherichia coli ATCC 25922 | 2.0 | 32.0 | 32.0 | 8.0 |
| Proteus mirabilis ATCC 12453 | 64.0 | >128.0 | 128.0 | 32.0 |
| Proteus mirabilis ATCC 43071 | 64.0 | >128.0 | >128.0 | 32.0 |
| Salmonella choleraesuis ATCC 13076 | 2.0 | 64.0 | 32.0 | 8.0 |
| Shigella flexneri ATCC 12022 | 1.0 | 32.0 | 32.0 | 4.0 |
| Yersinia enterocolitica ATCC 9610 | 1.0 | 16.0 | 16.0 | 4.0 |
| Haemophilus influenzae ATCC 49247 | 0.5 | 2.0 | 4.0 | 1.0 |
| Haemophilus influenzae ATCC 49766 | 1.0 | 4.0 | 8.0 | 1.0 |
| Pseudomonas aeruginosa ATCC 25619 | 64.0 | >128.0 | >128.0 | 32.0 |

The process is illustrated by the following Examples, which do not limit the scope of the invention in any way.

EXAMPLE 1

Preparation of 6-O-methylerythromycin A 9(E)- and 9(Z)-oxime

Method A

6-O-methylerythromycin A (2.0 g, 0.003 mole) in methanol (100 ml) was heated to the reflux temperature, hydroxylamine hydrochloride (2.0 g, 0.03 mole) and sodium carbonate (0.2 g, 0.002 mole) were added and it was heated under reflux while stirring for 3 hours. Then repeatedly the same amounts of hydroxylamine hydrochloride and sodium carbonate were added and it was heated under reflux for further 6 hours. Methanol was evaporated at reduced pressure and then water (200 ml) and chloroform (100 ml) were added, pH was adjusted to 9.8, the layers were separated and the aqueous layer was extracted twice more with chloroform. The combined organic extracts were dried over potassium carbonate, filtered and evaporated at reduced pressure, yielding 2.0 g of a mixture of the title products. By chromatography on silica gel column using the system methylene chloride-methanol-conc. ammonium hydroxide 90:9:1.5, 0.63 g of chromatographically homogeneous 6-O-methyl-erythromycin A 9(E)-oxime with Rf 0.446 and 0.61 g of chromatographically homogeneous 6-O-methylerythromycin A 9(Z)-oxime with Rf 0.355 were obtained.

9(E)-oxime:

Rf 0.418, ethylacetate-(n-hexane)-diethylamine, 100:100:20 IR (KBr) cm$^{-1}$: 3449, 2974, 2939, 2832, 2788, 1735, 1638, 1459, 1379, 1348, 1169, 1112, 1054, 1012,957, 835, 755. $^1$H NMR (300 MHz, CDCl$_3$) δ: 5.11 (H-13), 4.95 (H-1"), 4.45 (H-1'), 4.03 (H-5"), 3.77 (H-8), 3.76 ((H-3), 3.75 (H-11), 3.66 (H-5), 3.48 (H-5'), 3.33 (3"-OCH$_3$), 3.24 (H-2'), 3.10 (6-OCH$_3$), 3.03 (H-4"), 2.89 (H-2), 2.57 (H-10), 2.45 (H-3'), 2.37 (H-2"a), 2.31/3'-N(CH$_3$)$_2$/, 1.93 (H-4), 1.93 (H-14a), 1.68 (H-4'a), 1.58 (H-2"b), 1.53 (H-7a), 1.48 (6-CH$_3$), 1.46 (H-14b), 1.31 (5"-CH$_3$), 1.25 (3"-CH$_3$), 1.23 (5'-CH$_3$), 1.20 (2-CH$_3$), 1.13 (10-CH$_3$), 1.13 (12-CH$_3$), 1.08 (4-CH$_3$), 1.00 (8-CH$_3$), 0.86 (15-CH$_3$). $^{13}$C NMR (75 MHz, CDCl$_3$) δ: 175.5 (C-1), 169.2 (C-9), 102.5 (C-1'), 95.7 (C-1"), 80.2 (C-5), 78.4 (C-6), 78.0 (C-3), 77.8 (C-4"), 76.5 (C-13), 73.8 (C-12), 72.4 (C-3"), 71.1 (C-2'), 70.0 (C-11), 68.2 (C-5'), 65.2 (C-5"), 64.9 (C-3'), 50.8 (6-OCH$_3$), 49.1 (3"-OCH$_3$), 44.7 (C-2), 40.1/3'-N(CH$_3$)$_2$/, 38.7 (C-4), 37.0 (C-7), 34.6 (C-2"), 32.3 (C-10), 29.4 (C-4'), 24.9 (C-8), 21.1 (5'-CH$_3$), 21.0 (3"-CH$_3$), 20.8 (C-14), 19.6 (6-CH$_3$), 18.3 (5"-CH$_3$), 18.2 (8-CH$_3$), 15.7 (12-CH$_3$), 15.6 (2-CH$_3$), 14.6 (10-CH$_3$), 10.2 (15-CH$_3$), 8.8 (4-CH$_3$).

9(Z)-oxime:

Rf 0.300, ethylacetate-(n-hexane)-diethylamine, 100:100:20 IR (KBr) cm$^{-1}$: 3433, 2973, 2939, 2832, 1733, 1638, 1459, 1379, 1348, 1286, 1169, 1114, 1054, 1011, 958, 892, 755. $^1$H NMR (300 MHz, CDCl$_3$) δ: 5.07 (H-13), 4.93 (H-1"), 4.43 (H-1'), 4.03 (H-5"), 3.98 (H-11), 3.77 (H-3), 3.62 (H-5), 3.48 (H-5'), 3.33 (3"-OCH$_3$), 3.21 (H-2'), 3.09 (6-OCH$_3$), 3.06 (H-4"), 2.88 (H-2), 2.74 (H-8), 2.65 (H-10), 2.45 (H-3'), 2.36 (H-2"a), 2.30/3'-N(CH$_3$)$_2$/, 1.96 (H-4), 1.94 (H-14a), 1.76 (H-14b), 1.67 (H-4'a), 1.59 (H-2"b), 1.58 (H-7a), 1.47 (H-7b), 1.38 (6-CH$_3$), 1.32 (10-CH$_3$), 1.31 (5"-CH$_3$), 1.25 (3"-CH$_3$), 1.24 (5'-CH$_3$), 1.19 (2-CH$_3$), 1.14 (12-CH$_3$), 1.07 (4-CH$_3$), 1.06 (8-CH$_3$), 0.84 (15-CH$_3$).

$^3$C NMR (75 MHz, CDCl$_3$) δ: 176.0 (C-1), 167.4 (C-9), 102.7 (C-1'), 96.0 (C-1"), 80.4 (C-5), 78.7 (C-6), 78.5 (C-3), 77.8 (C-4"), 76.9 (C-13), 74.7 (C-12), 72.6 (C-3"), 70.9 (C-2'), 70.3 (C-11), 68.4 (C-5'), 65.5 (C-5"), 65.3 (C-3'), 50.0 (6-OCH$_3$), 49.3 (3"-OCH$_3$), 45.0 (C-2), 41.0/3'-N(CH$_3$)$_2$/, 38.9 (C-4), 37.0 (C-7), 35.6 (C-8), 34.7 (C-2"), 34.1 (C-10), 28.9 (C-4'), 21.3 (3"-CH$_3$), 21.2 (5'-CH$_3$), 21.1 (C-14), 19.7 (6-CH$_3$), 19.6 (8-CH$_3$), 18.5 (5"-CH$_3$), 16.4 (12-CH$_3$), 15.7 (2-CH$_3$), 10.7 (10-CH$_3$), 10.4 (15-CH$_3$), 9.8 (15-CH$_3$).

Method B

6-O-methylerythromycin A (10.8 g, 0.014 mole) in methanol (800 ml) was heated to the reflux temperature, then hydroxylamine hydrochloride (27.0 g, 0.388 mole) and anhydrous sodium acetate (15.0 g, 0.183 mole) were added to the reaction solution in 4 portions within 10 hours and it was heated under reflux while stirring for further 8 hours. Methanol was evaporated at reduced pressure, water (1500 ml) and methylene chloride (200 ml) were added, and it was extracted by gradient extraction at pH 5.0 and 9.8. The combined organic extracts at pH 9.8 were dried over potassium carbonate, filtered and evaporated at reduced pressure, yielding 9.5 g of a mixture of the title products. By chromatography on a silica gel column using the system methylene chloride-methanol-conc. ammonium hydroxide 90:9:1.5, chromatographically homogeneous 6-O-methylerythromycin A 9(E)-oxime and 6-O-methylerythromycin A 9(Z)-oxime with physical-chemical constants identical to those of Method A were obtained.

EXAMPLE 2

Beckmann's rearrangement of 6-O-methylerythromycin A 9(E)-oxime

6-O-methylerythromycin A 9(E)-oxime from Example 1 (4.0 g, 0.005 mole) was dissolved in acetone (130 ml) and the solution was cooled to 0–5° C. Subsequently, solutions of p-toluenesulfochloride (2.6 g, 0.01 mole) in acetone (40 ml) and sodium hydrogen carbonate (0.830 g, 0.01 mole) in water (130 ml) were dropwise added thereto within 1 hour under stirring. The reaction mixture was stirred at room temperature for 8 hours, acetone was evaporated at reduced pressure and to the aqueous solution chloroform (40 ml) was added, whereupon it was extracted by gradient extraction at pH 5.0 and 9.0. The combined organic extracts at pH 9.0 were evaporated, yielding 2.8 g of 6-O-methyl-9a-aza-9a-homoerythromycin A.

Rf 0.218, ethylacetate-(n-hexane)-diethylamine, 100:100:20 IR (KBr) cm$^{-1}$: 3449, 2974, 2939, 2834, 1734, 1706, 1659, 1534, 1459, 1379, 1274, 1169, 1111, 1053, 1011,958. $^1$H NMR (300 MHz, CDCl$_3$) δ: 6.12 (9a-CONH), 4.85 (H-1"), 4.68 (H-13), 4.45 (H-1'), 4.21 (H-3), 4.16 (H-10), 4.07 (H-5"), 3.75 (H-5), 3.49 (H-5'), 3.34 (3"-OCH$_3$), 3.32 (6-OCH$_3$), 3.22 (H-11), 3.20 (H-2'), 3.04 (H-4"), 2.83 (H-2), 2.43 (H-3'), 2.38 (H-2"a), 2.30/3'-N(CH$_3$)$_2$/, 2.22 (H-8), 2.07 (H-7a), 1.87 (H-4), 1.87 (H-14a), 1.67 (H-4'a), 1.57 (H-2"b), 1.57 (H-14b), 1.36 (6-CH$_3$), 1.33 (H-7b), 1.32 (5"-CH$_3$), 1.25 (3"-CH$_3$), 1.24 (H-4'b), 1.23 (5'-CH$_3$), 1.23 (2-CH$_3$), 1.18 (12-CH$_3$), 1.16 (10-CH$_3$), 1.09 (8-CH$_3$), 1.02 (4-CH$_3$), 0.89 (15-CH$_3$). $^{13}$C NMR (75 MHz, CDCl$_3$) δ: 179.5 (C-1), 177.3 (C-9), 102.5 (C-1'), 94.9 (C-1"), 79.1 (C-6), 78.5 (C-5), 77.7 (C-4"), 77.7 (C-13), 75.9 (C-3), 73.9 (C-12), 72.5 (C-3"), 72.6 (C-11), 70.7 (C-2'), 68.2 (C-5'), 65.3 (C-5"), 65.1 (C-3'), 51.0 (6-OCH$_3$), 49.1 (3"-OCH$_3$), 45.1 (C-10), 44.5 (C-2), 41.3 (C-4), 40.0/3'-N(CH$_3$)$_2$/, 39.6 (C-7), 35.4 (C-8), 34.4 (C-2"), 28.8 (C-4'), 21.1 (5'-CH$_3$), 21.0 (3"-CH$_3$), 20.3 (C-14), 20.2 (6-CH$_3$), 19.1 (8-CH$_3$), 18.1 (5"-CH$_3$), 15.9 (12-CH$_3$), 14.6 (2-CH$_3$), 13.4 (10-CH$_3$), 10.7 (15-CH$_3$), 8.7 (4-CH$_3$).

EXAMPLE 3

Beckmann's rearrangement of 6-O-methylerythromycin A 9(Z)-oxime

6-O-methylerythromycin A 9(Z)-oxime from Example 1 (1.4 g, 0.002 mole) was dissolved in acetone (50 ml) and the solution was cooled to 0–5° C. Subsequently, solutions of p-toluenesulfochloride (1.84 g, 0.014 mole) in acetone (56 ml) and sodium hydrogen carbonate (1.16 g, 0.014 mole) in water (180 ml) were dropwise added thereto within 1 hour under stirring. The reaction mixture was stirred at room temperature for 2 hours, acetone was evaporated at reduced pressure and to the aqueous solution chloroform (70 ml) was added, whereupon it was extracted by gradient extraction at pH 5.0 and 9.0. The combined organic extracts at pH 9.0 were evaporated, yielding 0.80 g of product, which, if appropriate, was purified by chromatography on a silica gel column using the system methylene chloride-methanol-conc. ammonium hydroxide 90:9:1.5, yielding 6-O-methyl-8a-aza-8a-homoerythromycin A with the following physical-chemical constants:

Rf 0.152, ethylacetate-(n-hexane)-diethylamine, 100:100:20 IR (KBr) cm$^{-1}$: 3442, 2974, 2938, 2833, 1736, 1648, 1535, 1459, 1379, 1284, 1169, 1110, 1055, 1013, 960, 902. $^1$H NMR (300 MHz, CDCl$_3$) δ: 5.78 (8a-CONH), 5.02 (H-1"), 4.96 (H-13), 4.41 (H-1'), 4.19 (H-8), 4.02 (H-5"), 3.96 (H-3), 3.69 (H-5), 3.51 (H-11), 3.47 (H-5'), 3.32 (3"-OCH$_3$), 3.18 (H-2'), 3.16 (6-OCH$_3$), 3.02 (H-4"), 2.68 (H-2), 2.44 (H-3'), 2.35 (H-2"a), 2.29/3'-N(CH$_3$)$_2$/, 2.22 (H-10), 1.92 (H-4), 1.91 (H-14a), 1.68 (H-7a), 1.64 (H-4'a), 1.56 (H-2"b), 1.53 (H-7b), 1.47 (H-14b), 1.39 (6-CH$_3$), 1.29 (5"-CH$_3$), 1.24 (3"-CH$_3$), 1.23 (5'-CH$_3$), 1.20 (2-CH$_3$), 1.18 (10-CH$_3$), 1.13 (12-CH$_3$), 1.13 (8-CH$_3$), 1.07 (4-CH$_3$), 0.88 (15-CH$_3$). $^{13}$C NMR (75 MHz, CDCl$_3$) δ: 177.0 (C-1), 174.3 (C-9), 102.9 (C-1'), 95.1 (C-1"), 80.1 (C-5), 78.6 (C-6), 77.9 (C-4"), 77.2 (C-3), 76.7 (C-13), 74.0 (C-12), 72.6 (C-3"), 70.4 (C-2'), 70.1 (C-11), 68.7 (C-5'), 65.4 (C-3'), 65.2 (C-5"), 51.5 (6-OCH$_3$), 49.1 (3"-OCH$_3$), 45.4 (C-2), 42.6 (C-7), 42.1 (C-4), 41.8 (C-10), 40.6 (C-8), 40.0/3'-N(CH$_3$)$_2$/, 34.5 (C-2"), 28.3 (C-4'), 23.5 (6-CH$_3$), 21.3 (C-14), 21.2 (12-CH$_3$), 21.1 (5'-CH$_3$), 21.1 (3"-CH$_3$), 17.9 (5"-CH$_3$), 15.8 (8-CH$_3$), 14.8 (2CH$_3$), 10.8 (15-CH$_3$), 9.2 (10-CH$_3$), 9.1 (4-CH$_3$).

EXAMPLE 4

3-decladinosyl-3-oxy-6-O-methyl-9a-aza-9a-homoerythromycin A

The substance from Example 2 (1.5 g, 0.002 mole) was dissolved in 0.25 N hydrochloric acid (40 ml) and it was left to stand for 24 hours at room temperature. To the reaction mixture methylene chloride (30 ml) (pH 1.8) was added and the pH of the mixture was adjusted to 9.0 with conc. ammonia, the layers were separated and the aqueous layer was extracted twice more with methylene chloride (30 ml). The combined organic extracts were washed with a 10% aqueous solution of sodium hydrogen carbonate and water and then evaporated, yielding 1.3 g of a crude product, which, if appropriate, was purified by chromatography on a silica gel column using the system methylene chloride-methanol-conc. ammonium hydroxide 90:9:1.5. From 0.9 g of the crude product there were isolated 0.65 g of chromatographically homogeneous 3-decladinosyl-3-oxy-6-O-methyl-9a-aza-9a-homoerythromycin A with the following physical-chemical constants:

Rf 0.152, ethylacetate-(n-hexane)-diethylamine, 100:100:20 IR (KBr) cm$^{-1}$: 3438, 2973, 2939, 2879, 2788, 1702, 1658, 1535, 1458, 1373, 1329, 1270, 1173, 1112, 1050, 985, 958, 937. $^1$H NMR (300 MHz, CDCl$_3$) δ: 7.16 (9a-CONH), 4.63 (H-13), 3.81 (H-5), 4.45 (H-1'), 4.13 (H-10), 3.78 (H-3), 3.55 (H-5'), 3.30 (6-OCH$_3$), 3.25 (H-2'), 3.16 (H-11), 2.66 (H-2), 2.51 (H-3'), 2.39 (H-8), 2.26/3'-N (CH$_3$)$_2$/, 2.05 (H-4), 1.92 (H-14a), 1.84 (H-7a), 1.68 (H-4'a), 1.57 (H-14b), 1.43 (H-7b), 1.38 (6-CH$_3$), 1.33 (2-CH$_3$), 1.26 (5'-CH$_3$), 1.26 (H-4'b), 1.20 (10-CH$_3$), 1.12 (12-CH$_3$), 1.11 (8-CH$_3$), 1.01 (4-CH$_3$), 0.91 (15-CH$_3$). $^{13}$C NMR (75 MHz, CDCl$_3$) δ: 179.3 (C-1), 176.9 (C-9), 106.4 (C-1'), 88.1 (C-5), 79.1 (C-6), 78.7 (C-13), 78.0 (C-3), 73.8 (C-12), 73.9 (C-11), 70.2 (C-2'), 69.7 (C-5'), 65.4 (C-3'), 49.9 (6-OCH$_3$), 45.6 (C-10), 43.9 (C-2), 40.8 (C-7), 39.9/3'-N(CH$_3$)$_2$, 35.6 (C-4), 32.8 (C-8), 27.8 (C-4'), 20.9 (5'-CH$_3$), 20.5 (C-14), 18.3 (6-CH$_3$), 17.4 (8-CH$_3$), 15.8 (12-CH$_3$), 15.9 (2-CH$_3$), 14.8 (10-CH$_3$), 10.7 (15-CH$_3$), 7.5 (4-CH$_3$).

EXAMPLE 5

3-decladinosyl-3-oxy-6-O-methyl-8a-aza-8a-homoerythromycin A

From the substance (1.5 g, 0.002 mole) of Example 3 there were obtained, according to the process described in Example 4, 1.2 g of a crude product, which, if appropriate, was purified by chromatography on a silica gel column using the system methylene chloride-methanol-conc. ammonium hydroxide 90:9:1.5, yielding chromatographically homogeneous 3-decladinosyl-3-oxy-6-O-methyl-8a-aza-8a-homoerythromycin A with the following physical-chemical constants:

Rf 0.195, chloroform-methanol-conc. ammonium hydroxide, 6:1:0.1 IR (KBr) cm$^{-1}$: 3438, 2974, 2939, 2788, 1733, 1648, 1535, 1458, 1378, 1263, 1165, 1113, 1075, 1050, 985, 958, 937. $^1$H NMR (300 MHz, CDCl$_3$) δ: 5.58 (9a-CONH), 5.09 (H-13), 4.38 (H-1'), 3.76 (H-5), 3.92 (H-8), 3.80 (H-3), 2.64 (H-2), 3.54 (H-5'), 3.47 (H-11), 3.25 (H-2'), 2.11 (H-4), 3.12 (6-OCH$_3$), 2.48 (H-3'), 2.38 (H-10), 2.25/3'-N(CH$_3$)$_2$/, 1.94 (H-14a), 2.11 (H-7a), 1.66 (H-4'a), 1.51 (H-7b), 1.50 (H-14b), 1.31 (2-CH$_3$), 1.39 (6-CH$_3$), 1.12 (4-CH$_3$), 1.26 (5'-CH$_3$), 1.26 (H-4'b), 1.20 (10-CH$_3$), 1.25 (8-CH$_3$), 1.13 (12-CH$_3$), 0.88 (15-CH$_3$). $^{13}$C NMR (75 MHz, CDCl$_3$) δ: 176.0 (C-1), 174.4 (C-9), 106.1 (C-1'), 89.6 (C-5), 77.3 (C-6), 75.8 (C-13), 78.3 (C-3), 74.3 (C-12), 70.3 (C-11), 69.9 (C-2'), 69.4 (C-5'), 64.9 (C-3'), 49.7 (6-OCH$_3$), 42.1 (C-10), 43.8 (C-2), 41.7 (C-7), 39.9/3'-N(CH$_3$)$_2$/, 35.2 (C-4), 42.4 (C-8), 27.4 (C-4'), 22.3 (5'-CH$_3$), 20.9 (C-14), 20.4 (6-CH$_3$), 20.5 (8-CH$_3$), 15.7 (12-CH$_3$), 15.2 (2-CH$_3$), 9.5 (10-CH$_3$), 10.1 (15-CH$_3$), 7.50 (4-CH$_3$).

EXAMPLE 6

3-decladinosyl-3-oxy-6-O-methyl-9a-aza-9a-homoerythromycin A 2'-O-acetate

To a solution of 3-decladinosyl-3-oxy-6-O-methyl-9a-aza-9a-homoerythromycin A (0.750 g, 0.0012 mole) from Example 4 in methylene chloride (25 ml), sodium hydrogen carbonate (0.440 g, 0.0052 mole) and acetic acid anhydride (0.128 ml, 0.0013 mole) were added and it was stirred for 3 hours at room temperature. To the reaction mixture a saturated solution of sodium hydrogen carbonate (30 ml) was added, the layers were separated and the aqueous portion was again extracted with methylene chloride (2×20 ml). The combined organic extracts were washed successively with a saturated solution of hydrogen carbonate and water and evaporated, yielding 0.750 g of a crude title product with the following physical-chemical constants:

Rf 0.403 chloroform-methanol-conc. ammonium hydroxide, 6:1:0.1 IR (KBr) cm$^{-1}$: 3455, 2974, 2940, 2880, 2787, 1748, 1702, 1658, 1540, 1459, 1376, 1239, 1173, 1112, 1061, 986, 958, 937, 904.

EXAMPLE 7

3-decladinosyl-3-oxy-6-O-methyl-8a-aza-8a-homoerythromycin A 2'-O-acetate

To a solution of 3-decladinosyl-3-oxy-6-O-methyl-9a-aza-9a-homoerythromycin A (1.5 g, 0.0024 mole) from Example 5 in methylene chloride (40 ml), sodium hydrogen carbonate (0.88 g, 0.01 mole) and acetic acid anhydride (0.250 ml, 0.0025 mole) were added and then, according to the process described in Example 6, there were obtained 1.4 g of the title product with the following physical-chemical constants:

Rf 0.423, chloroform-methanol-conc. ammonium hydroxide, 6:1:0.1 IR (KBr) cm$^{-1}$: 3394, 2972, 2939, 2784, 1736, 1649, 1542, 1459, 1376, 1262, 1165, 1085, 1059, 986, 958, 904.

EXAMPLE 8

3-decladinosyl-3-oxo-6-O-methyl-9a-aza-9a-homoerythromycin A

To a solution of 3-decladinosyl-3-oxy-6-O-methyl-9a-aza-9a-homoerythromycin A 2'-O-acetate (0.760 g, 0.0012 mole) from Example 6 in methylene chloride (15 ml), dimethyl sulfoxide (1.27 ml) and N,N-dimethylaminopropyl-ethyl-carbodiimid (1.335 g, 0.007 mole) were added. The reaction mixture was cooled to 15° C. and then, under stirring and maintaining this temperature, a solution of pyridinium trifluoroacetate (1.37 g, 0.007 mole) in methylene chloride (5 ml) was gradually added dropwise within 30 minutes. The temperature of the reaction mixture was gradually increased to room temperature, the stirring was continued for further 3 hours and then the reaction was ceased by the addition of a saturated solution of NaCl (20 ml) and methylene chloride (20 ml). After alkalizing the reaction mixture to pH 9.5 with 2N NaOH, it was extracted with $CH_2Cl_2$, the organic extracts were successively washed with a saturated solution of NaCl, $NaHCO_3$ and water and then dried over $K_2CO_3$. After filtration and evaporation of methylene chloride at reduced pressure, 0.800 g of an oily residue were obtained. The oily residue was subjected to the methanolysis (30 ml of methanol) within 24 hours at room temperature. Methanol was evaporated at reduced pressure and the obtained residue (0.625 g) was purified by low-pressure chromatography on a silica gel column using the solvent system dichloromethane-methanol-conc. ammonium hydroxide 90:9:0.5. By evaporation of the combined extracts with Rf 0.235, there was obtained a chromatographically homogeneous title product with the following physical-chemical constants:

Rf 0.235, methylene chloride-methanol-conc. ammonium hydroxide 90:9:0.5 IR (KBr) $cm^{-1}$: 3438, 2975, 2939, 2878, 2787, 1744, 1655, 1530, 1458, 1380, 1340, 1304, 1169, 1111, 1075, 1051, 986, 959, 940. $^1H$ NMR (300 MHz, $CDCl_3$) δ: 6,63 (9a-CONH), 4.64 (H-13), 4.49 (H-5), 4.41 (H-1'), 4.20 (H-10), 3.90 (H-2), 3.64 (H-5'), 3.34 (H-11), 3.20 (H-2'), 3.07 (6-$OCH_3$), 3.02 (H-4), 2.51 (H-3'), 2.30 (H-8), 2.27/3'-N($CH_3$)$_2$/, 1.94 (H-14a), 1.94 (H-7a), 1.69 (H-4'a), 1.63 (H-14b), 1.42 (H-7b), 1.40 (2-$CH_3$), 1.30 (5'-$CH_3$), 1.29 (4-$CH_3$), 1.26 (6-$CH_3$), 1.25 (H-4'b), 1.22 (12-$CH_3$), 1,19 (10-$CH_3$), 1.10 (8-$CH_3$), 0.91 (15-$CH_3$). $^{13}C$ NMR (75 MHz, $CDCl_3$) δ 206.8 (C-3), 177.3 (C-1), 173.8 (C-9), 102.6 (C-1'), 79.3 (C-13), 78.4 (C-6), 74.4 (C-5), 73.9 (C-12), 73.1 (C-11), 70.0 (C-2'), 69.1 (C-5'), 65.5 (C-3'), 50.1 (6-$OCH_3$), 49.0 (C-2), 46.2 (C-4), 45.3 (C-10), 40.3 (C-7), 40.0/3'-N($CH_3$)$_2$/, 34.6 (C-8), 28.3 (C-4'), 21.0 (6-$CH_3$), 20.7 (C-14), 19.6 (5'-$CH_3$), 18.6 (8-$CH_3$), 15.9 (12-$CH_3$), 14.1 (2-$CH_3$), 13.9 (10-$CH_3$), 13.9 (4-$CH_3$), 10.7 (15-$CH_3$).

EXAMPLE 9

3-decladinosyl-3-oxo-6-O-methyl-8a-aza-8a-homoerythromycin A

To a solution of 3-decladinosyl-3-oxy-6-O-methyl-8a-aza-8a-homoerythromycin A 2'-O-acetate (1.4 g, 0.0022 mole) from Example 7 in methylene chloride (30 ml), dimethyl sulfoxide (2.5 ml) and N,N-dimethylaminopropyl-ethyl-carbodiimid (2.7 g, 0.014 mole) were added. The reaction mixture was cooled to 15° C. and, under stirring and maintaining this temperature, a solution of pyridinium trifluoroacetate (2.7 g, 0.014 mole) in methylene chloride (10 ml) was gradually added dropwise within 30 minutes. According to the process described in Example 8, there were obtained 1.1 g of the title product with the following physical-chemical constants:

IR (KBr) $cm^{-1}$: 3435, 2975, 2939, 2879, 2788, 1746, 1648, 1542, 1458, 1379, 1339, 1302, 1166, 1111, 1076, 1052,989,960,918. $^1H$ NMR (300 MHz, $CDCl_3$) δ: 5.89 (9a-CONH), 5.08 (H-13), 4.42 (H-1'), 4.27 (H-5), 4.03 (H-8), 3.78 (H-2), 3.60 (H-5'), 3.58 (H-11), 3.18 (H-2'), 3.05 (H-4), 2.91 (6-$OCH_3$), 2.49 (H-3'), 2.39 (H-10), 2.27/3'-N ($CH_3$)$_2$/, 1.96 (H-14a), 1.68 (H-7a), 1.68 (H-4'a), 1.50 (H-14b), 1.41 (2-$CH_3$), 1.32 (6-$CH_3$), 1.30 (4-$CH_3$), 1.25 (5'-$CH_3$), 1.23 (H-4'b), 1.20 (10-$CH_3$), 1.19 (8-$CH_3$), 1.17 (12-$CH_3$), 0.88 (15-$CH_3$). $^{13}C$ NMR (75 MHz, $CDCl_3$) δ: 206.2 (C-3), 170.0 (C-9), 174.6 (C-1), 103.1 (C-1'), 78.2 (C-6), 77.9 (C-5), 77.5 (C-13), 74.1 (C-12), 70.6 (C-11), 70.0 (C-2'), 69.1 (C-5'), 65.5 (C-3'), 50.5 (6-$OCH_3$), 50.4 (C-2), 47.6 (C-4), 42.2 (C-10), 42.1 (C-7), 41.6 (C-8), 39.9/3'-N($CH_3$)$_2$/, 28.0 (C-4'), 22.8 (8-$CH_3$), 21.2 (C-14), 20.8 (5'-$CH_3$), 20.1 (6-$CH_3$), 16.1 (12-$CH_3$), 15.4 (2-$CH_3$), 14.4 (4-$CH_3$), 10.5 (15-$CH_3$), 10.1 (10-$CH_3$).

What is claimed is:

1. Compound represented by the formula (I)

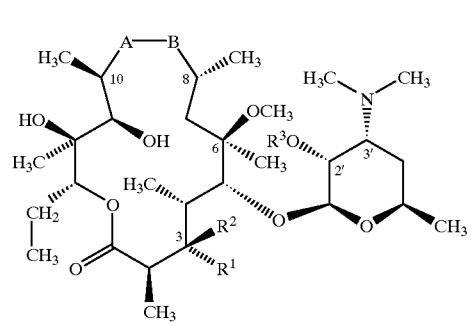

and its pharmaceutically acceptable addition salts with inorganic and organic acids, wherein A represents NH group and B at the same time represents C=O group, or A represents C=O group and B at the same time represent NH group, $R^1$ represents OH group, L-cladinosyl group of the formula (II)

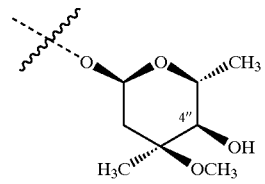

or together with $R^2$ represents ketone, $R^2$ represents hydrogen or together with $R^1$ represents ketone, $R^3$ represents hydrogen or $C_1$–$C_4$ alkanoyl group.

2. Compound according to claim 1, characterized in that A represents NH group, B represents C=O group, $R^1$ represents L-cladinosyl group of the formula (II), $R^2$ and $R^3$ are the same and represent hydrogen.

3. Compound according to claim 1, characterized in that A represents C=O group, B represents NH group, $R^1$ represents L-cladinosyl group of the formula (II) and $R^2$ and $R^3$ are the same and represent hydrogen.

4. Compound according to claim 1, characterized in that A represents NH group, B represents C=O group, $R^1$ represents OH group and $R^2$ and $R^3$ are the same and represent hydrogen.

5. Compound according to claim 1, characterized in that A represents C=O group, B represents NH group, $R^1$ represents OH group and $R^2$ and $R^3$ are the same and represent hydrogen.

6. Compound according to claim 1, characterized in that A represents NH group, B represents C=O group, $R^1$ represents OH group, $R^2$ is hydrogen and $R^3$ represents $C_1$–$C_4$ alkanoyl group.

7. Compound according to claim 6, characterized in that $R^3$ represents acetyl group.

8. Compound according to claim 1, characterized in that A represents C=O group, B represents NH group, $R^1$ represents OH group, $R^2$ is hydrogen and $R^3$ represents $C_1$–$C_4$ alkanoyl group.

9. Compound according to claim 8, characterized in that $R^3$ represents acetyl group.

10. Compound according to claim 1, characterized in that A represents NH group, B represents C=O group, $R^1$ and $R^2$ together represent ketone and $R^3$ is hydrogen.

11. Compound according to claim 1, characterized in that A represents C=O group, B represents NH group, $R^1$ and $R^2$ together represent ketone and $R^3$ is hydrogen.

12. Process for the preparation of a compound of the formula (I)

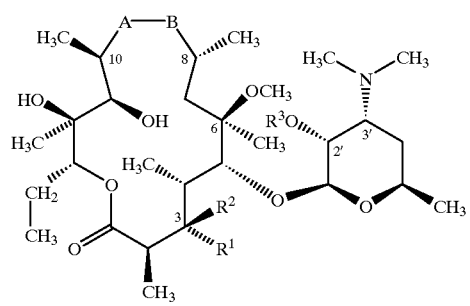

(I)

and its pharmaceutically acceptable addition salts with inorganic and organic acids, wherein A represents NH group and B at the same time represents C=O group, or A represents C=O group and B at the same time represents NH group, $R^1$ represents OH group, L-cladinosyl group of the formula (II)

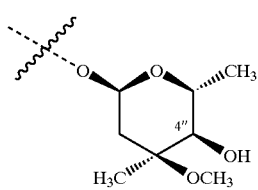

(II)

or together with $R^2$ represents ketone, $R^2$ represents hydrogen or together with $R^1$ represents ketone, $R^3$ represents hydrogen or $C_1$–$C_4$ alkanoyl group, characterized in that 6-O-methylerythromycin A of the formula (III)

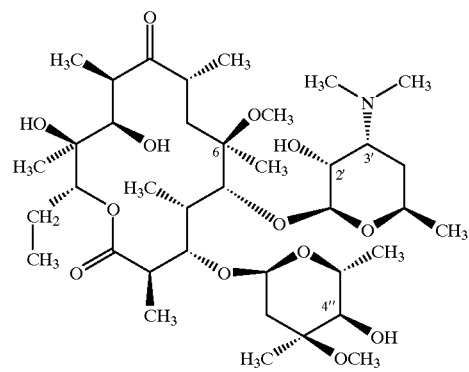

(III)

is subjected to a reaction with hydroxylamine hydrochloride in the presence of appropriate inorganic or organic base yielding a mixture of 6-O-methylerythromycin A 9(E)- and 9(Z)-oximes of the formula (IV)

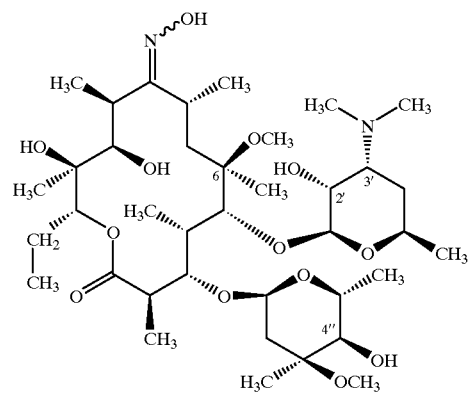

(IV)

which, if appropriate, is subjected to separation on a silica gel column using the system methylene chloride-methanol-conc. ammonium hydroxide 90:9:1.5, yielding chromatographically homogeneous 6-O-methyl-erythromycin A 9(E)-oxime with Rf 0.446 of the formula (IVa)

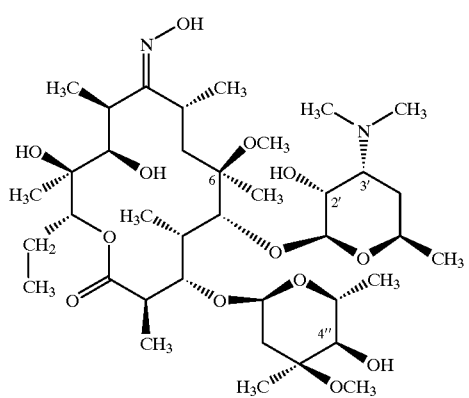

(IVa)

and chromatographically homogeneous 6-O-methylerythromycin A 9(Z)-oxime with Rf 0.355 of the formula (IVb)

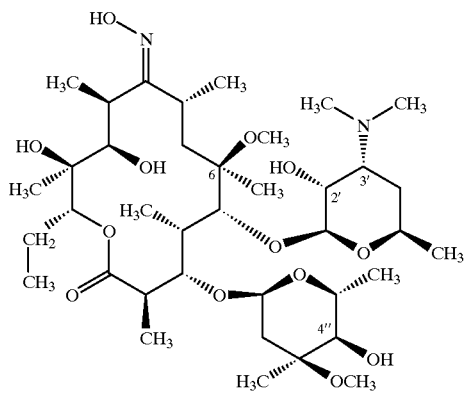
(IVb)

and then to the reaction of Beckmann's rearrangement with an arylsulfonyl halide, in the presence of an inorganic base in a solvent or solvent mixture inert to the reaction yielding in the case of 6-O-methyl-erythromycin A 9(E)-oxime of the formula (IVa) a compound of the formula (I), wherein A represents NH group, B represents C=O group, $R^1$ represents L-cladinosyl group of the formula (II) and $R^2$ and $R^3$ are the same and represent hydrogen, or in the case of 6-O-methylerythromycin A 9(Z)-oxime of the formula (IVb) a compound of the formula (I), wherein A represents C=O group, B represents NH group, $R^1$ represents L-cladinosyl group and $R^2$ and $R^3$ are the same and represent hydrogen, which is then subjected to the action of a diluted inorganic acid, at a room temperature, yielding a compound of the formula (I), wherein A represents NH group and B at the same time represents C=O group, or A represents C=O group and B at the same time represents NH group, $R^1$ represents OH group and $R^2$ and $R^3$ are the same and represent hydrogen, which is then subjected to the reaction of selective acylation with an anhydride of carboxylic acid with up to 4 carbon atoms in an inert organic solvent, yielding a compound of formula (I), wherein A represents NH group and B at the same time represents C=O group, or A represents C=O group and B at the same time represents NH group, $R^1$ is OH group, $R^2$ is hydrogen and $R^3$ is acetyl, which is then subjected to oxidation with a diamide, in the presence of dimethylsulfoxide and pyridinium trifluoroacetate as a catalyst in an inert organic solvent, at a temperature from 10° C. to room temperature, yielding a compound of the formula (I), wherein A represents NH group and B at the same time represents C=O group, or A represents C=O group and B at the same time represents NH group, $R^1$ together with $R^2$ represents ketone and $R^3$ is acetyl group, which is then subjected to the reaction of deacylation at 2'-position by solvolysis in a lower alcohol, at room temperature, yielding a compound of the formula (I), wherein A represents C=O group and B at the same time represents NH group, $R^1$ together with $R^2$ represent ketone and $R^3$ is hydrogen, which, if appropriate, is then subjected to the reaction with an inorganic or organic acid, yielding a pharmaceutically acceptable addition salt.

13. Pharmaceutical composition useful for treating bacterial infections in humans and animals, which contains antibacterially effective amounts of a compound of the formula (I) or of its pharmaceutically acceptable addition salts according to claim 1 in combination with a pharmaceutically acceptable carrier.

14. Method for treating bacterial infections in humans and animals, which comprises administering to a human or an animal, as required, antibacterially effective amounts of a compound of the formula (I) or of its pharmaceutically acceptable addition salts according to claim 1 in combination with a pharmaceutically acceptable carrier.

15. The process of claim 12 wherein the arylsulfonyl halide is p-toluenesulfonyl chloride.

16. The process of claim 12 wherein the inorganic base is sodium hydrogen carbonate.

17. The process of claim 12 wherein the solvent mixture inert to the reaction is acetone-water.

18. The process of claim 12 wherein the diluted inorganic acid is 0.25N hydrochloric acid.

19. The process of claim 12 wherein the anhydride is acetic acid anhydride in methylene chloride.

20. The process of claim 12 wherein the oxidation with the diamide comprises N,N-dimethylaminopropyl-ethyl-carbodiimide in the presence of dimethylsulfoxide and pyridinium trifluoracetate as catalyst in methylene chloride.

21. The process of claim 12 wherein the alcohol is methanol.

22. The process of claim 20 wherein the alcohol is methanol, the arylsulfonyl halide is p-toluenesulfonyl chloride, the inorganic base is sodium hydrogen carbonate in methylene chloride.

* * * * *